United States Patent [19]

Parker

[11] Patent Number: 5,045,632

[45] Date of Patent: Sep. 3, 1991

[54] NOVEL BIS(PHOSPHORANYLIDENE) AMMONIUM SALTS

[75] Inventor: Theodore L. Parker, Walnut Creek, Calif.

[73] Assignee: The Dow Chemical Company, Midland, Mich.

[21] Appl. No.: 630,146

[22] Filed: Dec. 19, 1990

Related U.S. Application Data

[63] Continuation of Ser. No. 358,297, May 25, 1989, abandoned.

[51] Int. Cl.$^5$ .................. C07C 303/00; C07C 307/00
[52] U.S. Cl. ......................................... 562/45; 562/30; 562/83; 562/91; 562/113; 564/82; 502/168
[58] Field of Search ...................... 564/82; 562/45, 30, 562/83, 91, 113; 502/168

[56] References Cited

U.S. PATENT DOCUMENTS

| | | |
|---|---|---|
| 4,197,390 | 4/1980 | Jackson . |
| 4,302,574 | 11/1981 | Doorakian et al. . |
| 4,354,015 | 10/1982 | Doorakian et al. . |
| 4,438,254 | 3/1984 | Doorakian et al. . |
| 4,602,070 | 7/1986 | Cavitt et al. . |
| 4,618,658 | 10/1986 | Hefner et al. . |
| 4,782,124 | 1/1988 | Hefner et al. . |
| 4,943,619 | 7/1990 | Bell et al. . |

Primary Examiner—Alan Siegel

[57] ABSTRACT

The invention is a novel bis(phosphoranylidene) ammonium salt useful as an initiator/catalyst in the reaction of oxirane groups in an epoxy resin with aromatic carbonate and/or ester linkages in monomeric, oligomeric, or polymeric carbonates, esters, or estercarbonates.

10 Claims, 1 Drawing Sheet

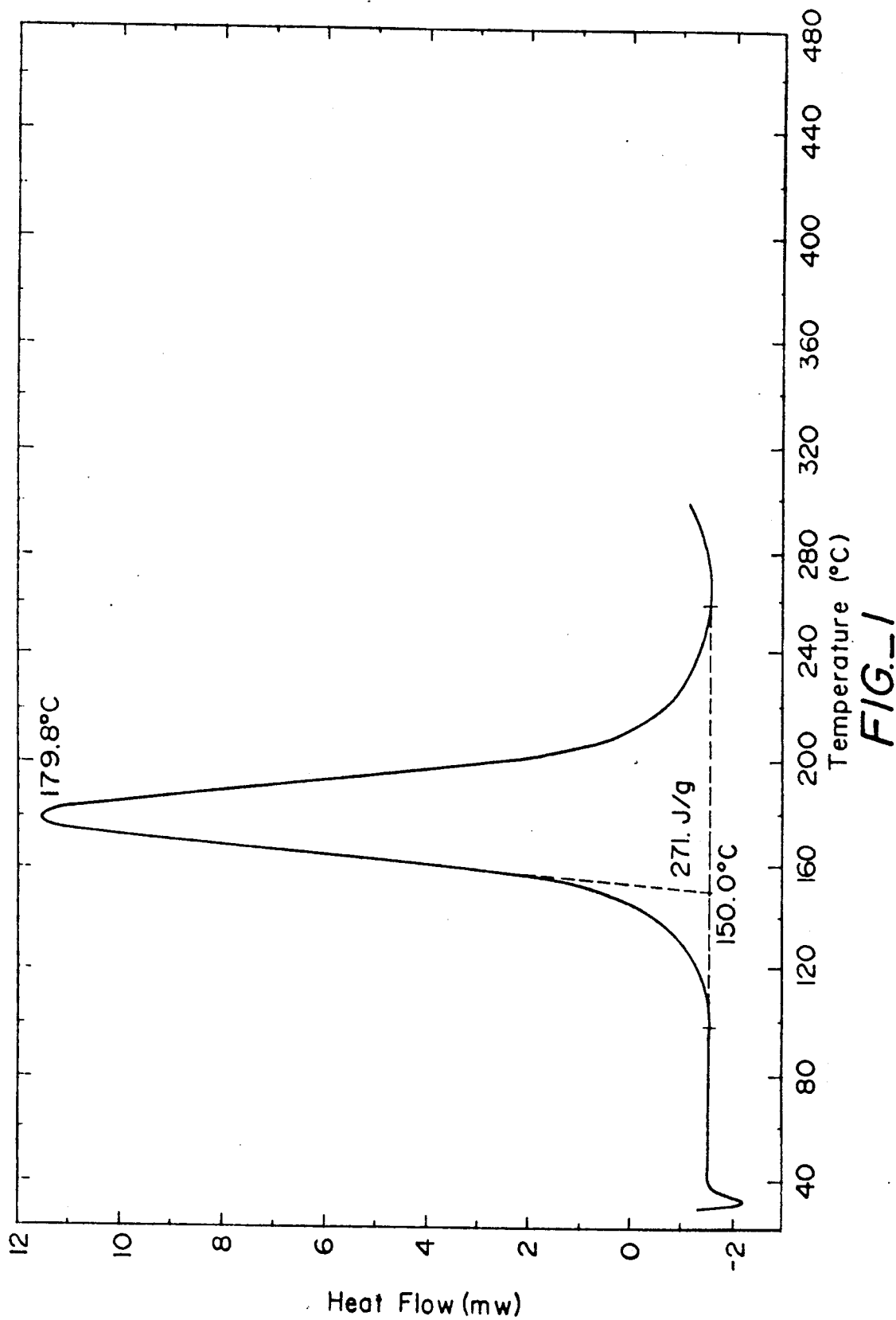

NOVEL BIS(PHOSPHORANYLIDENE) AMMONIUM SALTS

CROSS-REFERENCE TO RELATED APPLICATION

This is a continuation of application Ser. No. 07/358,297, filed May 25, 1989, now abandoned.

BACKGROUND OF THE INVENTION

This invention relates to novel bis(phosphoranylidene) ammonium salts. The bis(phosphoranylidene) ammonium salts of this invention are useful as initiators/catalysts in the reaction of epoxy resins with aromatic carbonate and/or ester linkages.

Conventionally cured epoxy resins contain residual secondary hydroxyl groups derived from oxirane ring opening by active hydrogens characteristic of such cured epoxy resins. The presence of such residual hydroxyl groups in conventionally cured epoxy resins impairs the performance and properties of the cured resin by providing a site for binding of water which acts to plasticize the cured resin composition, thus lowering tensile and flexural strength, lowering modulus, and increasing the dielectric constant. When oxirane groups are converted by reaction with carbonate or ester groups, no alcoholic hydroxyls are generated and the reaction can therefore be utilized to make epoxy-derived thermosets which absorb less water than conventially cured epoxies. Also, such thermosets, when prepared from carbonates, possess higher cross-link densities than conventionally cured epoxy resins, since each carbonate group reacts with two oxirane moieties. Consequentially, the epoxy/carbonate/ester cured product possesses improved temperature performance, increased water and solvent resistance, and improved dimensional stability.

The reaction of oxirane groups with aromatic carbonate and/or ester linkages requires use of an initiator/catalyst. Known types of initiators/catalysts found to be effective for this reaction typically show activity at relatively low temperatures of about 70° to about 125° C. and some decompose at temperatures in excess of about 200°–230° C. It has been discovered that in many cases, particularly when the compound containing aromatic carbonate and/or ester linkages is a polymer such as polycarbonate, polyester, or polyestercarbonate, the above mentioned initiators/catalysts do not allow a sufficient processing window for the melt blending of the initiator/catalyst and the epoxy resin with the compound containing carbonate and/or ester linkages.

What is needed is an active and effective initiator/catalyst for reaction of oxirane groups in epoxy resins with carbonate and/or ester linkages whose activity does not begin until higher temperatures of about 125° C. are reached. Furthermore, the initiator/catalytic activity should be substantially developed below the decomposition temperature of the reaction composition, which begins at about 300°–320° C. in air. The initiator/catalyst desirably does not initiate or speed up side reactions to such an extent that there does not result a cured product with a better combination of physical properties vis a vis the same epoxy resin per se cured with generally comparable types of initiators/catalysts.

SUMMARY OF THE INVENTION

The invention is a novel bis(phosphoranylidene) ammonium salt composition comprising a compound of Formula 1:

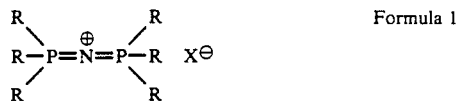

wherein

R is independently in each occurrence a $C_{1-20}$ monovalent hydrocarbon radical: and X is an anion selected from the group consisting of: $R^1SO_3^\ominus$, $R^2COO^\ominus$, $(R^3SO_2)_2N^\ominus$, $R^1SO_2^\ominus$, $R^1OHPO_3^\ominus$, $(R^1O)_2PO_2^\ominus$, $R^1HPO_3^\ominus$, $H_2PO_4^\ominus$, $HCO_3^\ominus$, $HSO_4^\ominus$, $PF_6^\ominus$, and $SbF_6^\ominus$, wherein $R^1$ is a $C_{1-12}$ monovalent hydrocarbon radical or $C_{1-12}$ monovalent halohydrocarbon radical, $R^2$ is a hydrogen radical, a $C_{2-12}$ monovalent hydrocarbon radical, or a $C_{1-12}$ monovalent halohydrocarbon radical, and $R^3$ is a $C_{1-12}$ monovalent hydrocarbon radical.

The novel bis(phosphoranylidene) ammonium salts of this invention are useful as initiators/catalysts in the reaction of oxirane groups in epoxy resins with aromatic carbonate and/or ester linkages. Such bis(phosphoranylidene) ammonium salts generally possess activity as initiators/catalysts at temperatures above about 125° C. and their activity is substantially developed below temperatures of about 300°–320° C. Use of such bis(phosphoranylidene) ammonium salt initiators/catalysts result in cured products possessing superior physical properties as compared with products obtained by use of compounds known to initiate/catalyze various adductions with oxiranes.

BRIEF DESCRIPTION OF THE DRAWING

FIG. 1 illustrates a DSC curve for the combination of bis(triphenylphosphoranylidene) ammonium methane sulfonate with a representative epoxy resin/polycarbonate mixture.

DETAILED DESCRIPTION OF THE INVENTION

The novel bis(phosphoranylidene) ammonium salts of this invention are useful as initiators/catalysts in the reaction of oxirane groups in epoxy resins with aromatic aromatic carbonate and/or ester linkages. The term initiator, also sometimes referred to as a coreactive catalyst, as used herein refers to an agent used to promote the reaction which is consumed by the reaction. The term catalyst, also sometimes referred to as a noncoreactive catalyst, as used herein refers to an agent used to promote the reaction which is not consumed by the reaction. The bis(phosphoranylidene) ammonium salts of this invention may act as initiators or catalysts depending upon the reactants. Bis(phosphoranylidene) ammonium salts are also sometimes referred to as bis(phosphine) iminium salts.

In the preceding Formula 1, R preferably is independently in each occurrence a monovalent radical of a $C_{1-12}$ alkyl, $C_{3-12}$ cycloalkyl, $C_{6-20}$ alkylaryl, or $C_{6-12}$ aryl: more preferably a $C_{1-6}$ alkyl, $C_{6-12}$ alkylaryl, or phenyl; even more preferably a $C_{1-4}$ alkyl, $C_{6-8}$ alkylaryl, or phenyl; most preferably ethyl, butyl, or phenyl.

X is preferably an anion selected from the group consisting of $R^1SO_3^\ominus$, $R^2COO^\ominus$, $(R^3SO_2)_2N^\ominus$, $R^1SO_2^\ominus$, $R^1OHPO_3^\ominus$, $(R^1O)_2PO_2^\ominus$, and $R^1HPO_3^\ominus$; more preferably $R^1SO_3^\ominus$, $R^2COO^\ominus$, and $(R^3SO_2)_2N^\ominus$; even more preferably $R^1SO_3^\ominus$ and $(R^3SO_2)_2N^\ominus$.

$R^1$ is preferably a monovalent radical of a $C_{1-12}$ alkyl, $C_{1-12}$ haloalkyl, $C_{3-12}$ cycloalkyl, $C_{3-12}$ halocycloalkyl, $C_{6-12}$ alkylaryl, $C_{6-12}$ haloalkylaryl, $C_{6-12}$ aryl, or $C_{6-12}$ haloaryl; more preferably a $C_{1-6}$ alkyl, $C_{1-6}$ haloalkyl, $C_{6-12}$ alkylaryl, $C_{6-12}$ haloalkylaryl, phenyl, or halophenyl. Preferred classes of halo-hydrocarbyl radicals include the residues of chlorohydrocarbons; more preferably a monovalent radical of a $C_{1-6}$ chloroalkyl, $C_{6-12}$ chloroalkylaryl, or chlorophenyl.

$R^2$ is preferably a monovalent radical of a $C_{2-12}$ alkyl, $C_{1-12}$ haloalkyl, $C_{3-12}$ cycloalkyl, $C_{3-12}$ halocycloalkyl, $C_{6-12}$ alkylaryl, $C_{6-12}$ haloalkylaryl, $C_{6-12}$ aryl, or $C_{6-12}$ haloaryl; more preferably a $C_{2-6}$ alkyl, $C_{1-6}$ haloalkyl, $C_{6-12}$ alkylaryl, $C_{6-12}$ haloalkylaryl, phenyl, or halophenol. Preferred classes of halohydrocarbyl radicals include the residues of chlorohydrocarbons; more preferably a monovalent radical of a $C_{1-6}$ chloroalkyl, $C_{6-12}$ chloroalkylaryl, or chlorophenyl.

$R^3$ is preferably a monovalent radical of a $C_{1-12}$ alkyl, $C_{3-12}$ cycloalkyl, $C_{6-12}$ alkylaryl, or $C_{6-12}$ aryl; more preferably a $C_{1-6}$ alkyl, $C_{6-12}$ alkylaryl, or phenyl.

As used herein, the terms halohydrocarbon, haloalkyl, halocycloalkyl, haloalkylaryl, and haloaryl refer respectively to partially or fully halosubstituted hydrocarbon, alkyl, cycloalkyl, alkylaryl, and aryl compounds or radicals.

The novel bis(phosphoranylidene) ammonium salts of this invention may be prepared by several methods, including an anion exchange method, which may be performed in aqueous, partially aqueous, or non-aqueous media, an hydroxide method, and a silver salt method.

In the aqueous anion exchange method, a first solution is formed by dissolving the appropriate bis(R-phosphoranylidene) ammonium halide, preferably the chloride, $R_6P_2N^\oplus Cl^\ominus$, or bromide, $R_6P_2N^\oplus Br^\ominus$, in an alcohol such as methanol. Water is then added to the solution. A second solution is formed by dissolving the appropriate alkali metal X salt, preferably the sodium salt, in water. The two solutions are mixed together, forming a precipitate which is the bis(R-phosphoranylidene) ammonium X salt, $R_6P_2N^\oplus X^\ominus$. The reaction preferably occurs at ambient temperatures. The precipitate is recovered by filtration, purified by water-washing, and dried.

In the non-aqueous anion exchange method, a first solution is prepared by dissolving the appropriate bis(R-phosphoranylidene)ammonium halide, preferably the chloride, $R^6P^2N^\oplus Cl^\ominus$, or bromide, $R^6P^2N^\oplus Br^\ominus$, in an alcohol such as methanol. A second solution is formed by dissolving the appropriate alkali metal X salt, preferably the sodium salt, in at least a stoichiometric amount or in excess, in an alcohol such as methanol. The solutions are mixed and the alcohol solvent removed by vacuum distillation. The residue is extracted with a second organic solvent, such as methylene chloride, which is then filtered and the product recovered by evaporation.

In the hydroxide method, a first solution is formed by dissolving the appropriate bis(R-phosphoranylidene) ammonium halide, preferably the chloride, $R_6P_2N^\oplus Cl^\ominus$, or bromide, $R_6P_2N^\oplus Br^\ominus$, in an alcohol such as methanol. The solution is chilled, preferably to a temperature below about 10° C. A second solution is formed by dissolving an alkali metal hydroxide, such as sodium or potassium hydroxide, in an alcohol such as methanol. The second solution is added dropwise with agitation to the first solution while maintaining the temperature below about 10° C. The mixture becomes a slurry which is filtered to recover the alkali metal halide precipitate. The remaining third solution is the bis(R-phosphoranylidene) ammonium hydroxide. A fourth solution is formed by dissolving the appropriate X acid in an appropriate solvent such as methanol. The fourth solution is then mixed with the bis(R-phosphoranylidene) ammonium hydroxide. The solution is then filtered and vacuum stripped to obtain a solid which is the bis(R-phosphoranylidene) ammonium X salt, $R_6P_2N^\oplus X^\ominus$.

In the silver salt method, the appropriate silver X salt is dissolved in a solvent such as acetone to form a first solution. The appropriate bis(R-phosphoranylidene) ammonium halide, preferably chloride, $R_6P_2N^\oplus Cl^\ominus$, or bromide, $R_6P_2N^\oplus Br^\ominus$, is dissolved in a solvent such as acetone to form a second solution. The two solutions are mixed and the silver halide precipitate which forms is removed by filtration. The remaining solution is then filtered and vacuum stripped to obtain a solid which is the bis(R-phosphoranylidene) ammonium X salt, $R_6P_2N^\oplus X^\ominus$.

The bis(phosphoranylidene) ammonium salts of this invention are useful as initiators/catalysts in the reaction of epoxy resins with compounds containing aromatic carbonate and/or ester linkages. Suitable epoxy resins include polyglycidyl ethers, esters, and amines. Preferred epoxy resins include those represented by Formulas 2-6.

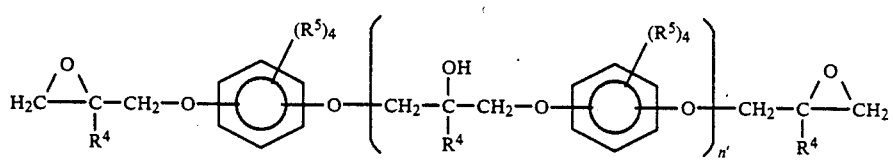

Formula 2

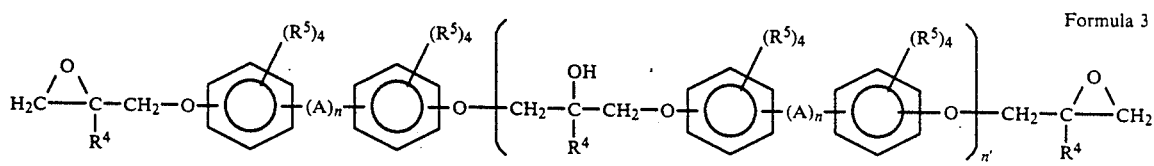

Formula 3

Formula 4

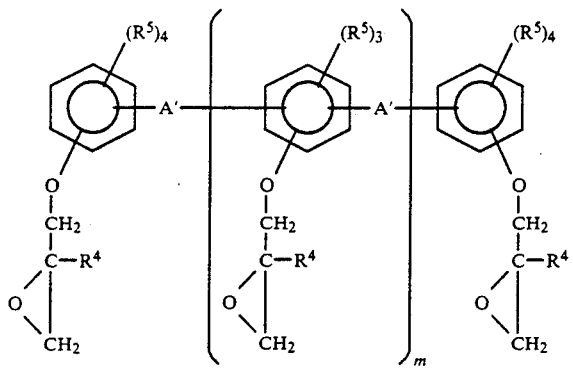

Formula 5

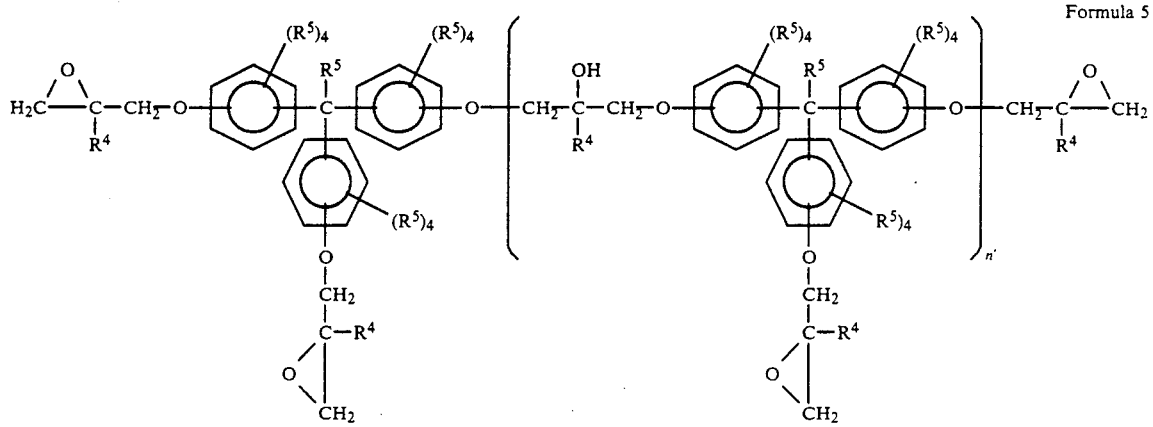

Formula 6

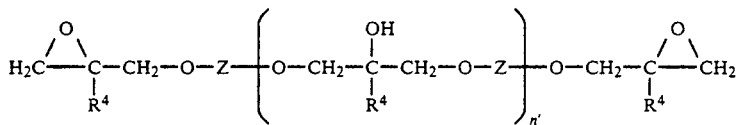

wherein A is a divalent hydrocarbon group having from 1 to about 12, preferably from 1 to about 6, more preferably from 1 to about 3, carbon atoms, $-C(CF_3)_2-$,

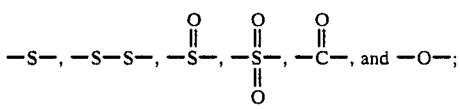

Z is a hydrocarbyl group containing from 1 to about 15 carbon atoms or a $-C(R^6)_2-C(R^6)_2-[O-C(R^6)_2-C(R^6)_2]_{m'}$ group; A' is a divalent hydrocarbon group having from 1 to about 3, preferably 1, carbon atoms or a

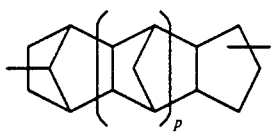

group: p has a value from zero to about 10, preferably from zero to 3: each $R^4$ is independently hydrogen, a hydrocarbyl or hydrocarbyloxy group having from 1 to 18 carbon atoms or a halogen, preferably chlorine or bromine: $R^5$ is independently hydrogen or a hydrocarbyl group having from 1 to about 3 carbon atoms; each $R^6$ is independently hydrogen or a hydrocarbyl group having from 1 to about 6 carbon atoms: n has a value from zero or 1; n' has a value from zero to about 40, preferably from 0.1 to about 5; m' has a value from 1 to about 100, preferably from 1 to about 25 and m has a value from about 0.001 to about 6. Such preferred epoxy resins are more fully described in U.S. Pat. No. 4,782,124, the relevant portions of which are incorporated herein by reference for all purposes which may be legally served thereby. The epoxy resins useful in this invention preferably do not contain hydroxyl groups in amounts which cause intolerably deleterious effects in the physical properties of the cured epoxy resin/carbonate/ester products. Epoxy resins containing significant amounts of hydroxyl groups may be used in this invention by first reacting/blocking such hydroxyl groups in the epoxy resins. For example, the hydroxyl groups in such epoxy resins may be reacted with carbonates, preferably of low molecular weight, via a transesterification reaction as described in U.S. Pat. Nos. 4,766,184 and 4,782,124, the relevant portions of which are incorporated herein by reference for all purposes which may be legally served thereby.

The aromatic carbonate and/or ester compounds may be monomeric, oligomeric, or polymeric. Polymeric compounds such as polycarbonates, polyesters, and polyestercarbonates are preferred. Polycarbonates, polyestercarbonates, and polyesters derived from bisphenol A are especially preferred. Each carbonate linkage reacts with two epoxide groups: each ester linkage reacts with one epoxide group. Other than stoichiometric ratios may be used depending upon the properties desired in the pre-cured and fully cured epoxy/carbonate/ester compositions.

The epoxy resin/carbonate/ester compositions described herein generally comprise relative amounts of epoxy resins and carbonate/ester compounds such as to provide from about 1 to about 5 oxirane groups per 2 carbonate and/or ester groups. The amount of initiator/catalyst used to promote the reaction is preferably between about 0.00075 and about 1.0 millimoles initiator/catalyst per gram of total epoxy/carbonate/ester composition. Generally, the use of an initiator/catalyst based on the conjugate base of a stronger acid, that is, acids with a lower pKa, results in higher activity temperatures, that is, secant on-set exotherm temperatures, for the initiator/catalyst. The initiators/catalysts of this invention preferably exhibit activity above about 125° C., more preferably above about 150° C. The initiator/catalyst activity is substantially developed below the decomposition temperature of the reaction composition, preferably below about 320° C., more preferably below about 300° C.

SPECIFIC EMBODIMENTS

The following Examples are for illustrative purposes only and are not meant to limit the scope of the invention in any manner inconsistent with the Claims of this patent.

EXAMPLE 1

Preparation of Bis(triphenylphosphoranylidene) Ammonium Hexafluorophosphate by Aqueous Anion Exchange Method A first solution is prepared by dissolving about 2.87 grams (0.005 mole) bis(triphenylphosphoranylidene) ammonium chloride (BTPPN-Cl) in about 5.00 grams anhydrous methanol, to which is added about 46.686 grams distilled water. A second solution is prepared by dissolving about 0.326 grams (0.002 mole) ammonium hexafluorophosphate in about 5.00 grams distilled water.

An aliquot of the BTPPN-Cl solution, about 10.91 grams (0.001 mole), is added to the ammonium hexafluorophosphate solution. A white precipitate is formed which is separated by vacuum filtration, washed with water, and dried under vacuum at about 80° C. for about 2 hours. The yield of product is about 5.36 grams (80 percent).

Elemental analysis of the product gives actual (calculated) results of C:59.62% (63.25%): H:4.23% (4.39%): N:1.82% (2.05%).

EXAMPLE 2

Preparation of Bis(triphenylphosphoranylidene) Ammonium Dihydrogen Phosphate by Aqueous Anion Exchange Method A solution is prepared by dissolving about 2.410 grams (0.02 mole) of sodium dihydrogenphosphate in about 15.00 grams distilled water. An aliquot of the BTPPN-Cl solution of Example 1, about 10.91 grams (0.001 mole), is added to the sodium dihydrogenphosphate solution. After the work-up described in Example 1, about 5.60 grams of white solid is isolated, representing a yield of about 91 percent.

Elemental analysis of the solid gives actual (calculated) results of C:66.61% (68.03%): H:5.12% (5.04%): N:2.14% (2.20%).

EXAMPLE 3

Preparation of Bis(triphenylphosphoranylidene) Ammonium Hydrogen Sulfate by Aqueous Anion Exchange Method A solution is prepared by dissolving about 0.0240 grams (2.0 mmole) of sodium bisulfate in about 5.00 grams distilled water. An aliquot of the BTPPN-Cl solution of Example 1, about 10.01 grams (1.0 mmole), is added to the sodium bisulfate solution. The mixture is placed in a refrigerator at about 5° C. where crystals form and are collected by vacuum filtration. Following the work-up of Example 1, about 3.42 grams of a white powder are obtained, representing a yield of about 55 percent.

EXAMPLE 14

Preparation of Bis(triphenylphosphoranylidene) Ammonium Trifluoroacetate by Aqueous Anion Exchange Method A solution is prepared by dissolving about 2.05 grams (15.0 mmole) sodium trifluoroacetate in about 10.0 grams methanol. A solution BTPPN-Cl, about 5.735 grams (10.0 mmole), dissolved in about 6.0 grams methanol is added to the sodium trifluoroacetate solution, followed by the addition of about 400 ml of water. A precipitate is formed which is separated by vacuum filtration. About 5.65 grams of white powder is obtained, resulting in a yield of about 87 percent.

EXAMPLE 5

Preparation of Bis(triphenylphosphoranylidene) Ammonium Dihydrogenphosphate by Hydroxide Method BTPPN-Cl, about 3.6174 grams (6.3 mmole), is dissolved in about 5.12 anhydrous methanol and chilled to below about 10° C. in an ice bath. A second solution, prepared by dissolving about 0.3963 grams (6.3 mmole) of 89.0 weight percent potassium hydroxide in about 1.5490 grams anhydrous methanol, is added dropwise with agitation to the BTPPN-Cl solution, maintaining the temperature below about 10° C. The mixture becomes a slurry which is vacuum filtered. The precipitate is washed with about 2.00 grams methanol and the filtrate and washing combined. This solution is titrated with perchloric acid in glacial acetic acid at about 0.5667 mmole/gram hydroxide. The precipitate is dried to give about 0.4241 grams powder, about 91 percent yield, as KCl.

To an aliquot of the BTPPN-OH solution, about., 3.593 grams (2.0 mmole), is added a solution of about 0.2386 grams (2.0 mmole) of phosphoric acid in about 4.0 grams anhydrous methanol. The solution is filtered at about 0.2 microns, vacuum stripped at about 50° C. to yield about 1.3405 grams of a white powder of purity about 89.5 weight percent, representing a yield of about 94 percent.

EXAMPLE 6

Preparation of Bis(triphenylphosphoranylidene) Ammonium p-Toluenesulfimidate by Hydroxide Method The method of Example 1 is used. To an aliquot of BTPPN-OH solution, about 3.593 grams (0.002 mole), is added a solution of about 0.650 grams (0.002 mole) p-toluenesulfimidate in about 8.0 grams tetrahydrofuran. The reaction mixture is vacuum stripped at about 50° C. to yield a white solid of about 1.6241 grams, about 94 percent yield. Purity by titration is about 95.1 weight percent.

EXAMPLE 7

Preparation of Bis(triphenylphosphoranylidene) Ammonium Methane Sulfonate by Non-Aqueous Anion Exchange Method A 125 ml flask is charged with about 30.07 grams anhydrous methanol, followed by about 2.88 grams (0.03 mole) methane sulfonic acid. Aqueous ammonium hydroxide, about 29.3 weight percent ammonia, about 1.741 grams (0.03 mole), is added dropwise.

To a vial is added about 0.5735 grams (1.0 mmole TPPN-Cl and about 5.0 grams anhydrous methanol. About 1.155 grams (3.0 mmole) of the ammonium methane sulfonate solution is added to the BTPPN-Cl solution. The solvent is stripped off under vacuum at about 100° C. The solid residue is extracted with about 15 ml methylene chloride and vacuum filtered through a fine glass frit. The remainder on the frit is washed with an additional about 10 ml methylene chloride, filtered, the filtrates combined and placed in a crystallizing dish on a warm hot plate. Following the evaporation of solvent, the crystalline solid is placed in a vacuum oven held at about 80° C. for about 1 hour to remove traces of solvent. The product is about 0.6087 grams white crystalline powder, representing a yield of about 96 percent.

Elemental analysis of the powder gives actual (calculated) results of C:68.76% (70.70%): H:5.29% (5.74%); N:2.27% (2.11%).

EXAMPLE 8

Preparation of Bis(triphenylphosphoranylidene) Ammonium p-Toluene Sulfonate by Non-Aqueous Anion Exchange Method The method of Example 7 is followed using a solution of about 1.0 mmole BTPPN-Cl in about 3.0 grams methanol which is mixed with a solution of about 3.0 mmole sodium p-toluene sulfonate in about 10.0 grams methanol. The product is about 0.5749 grams white crystalline powder, representing about 81 percent yield.

Elemental analysis of the product gives actual (calculated) results of C:72.69% (72.78%): H:5.33% (5.22%): N:1.91% (1.97%).

EXAMPLE 9

Preparation of Bis(triphenylphosphoranylidene) Ammonium Benzene Sulfonate by Non-Aqueous Anion Exchange Method The method of Example 7 is used on a 1.0 mmole scale starting from BTPPN-Cl and sodium benzene sulfonate for about a 91 percent yield of crystalline product.

Elemental analysis of the product gives actual (calculated) results of C:70.80% (72.52%); H:5.29% (5.04%): N:2.01% (2.01%).

EXAMPLE 10

Preparation of Bis(triphenylphosphoranylidene) Ammonium Chlorobenzene Sulfonate by Non-Aqueous Anion Exchange Method The method of Example 7 is used on a 1.0 mmole scale starting from BTPPN-Cl and sodium chlorobenzene sulfonate to yield about 93 percent crystalline product.

Elemental analysis of the product gives actual (calculated) results of C:69.34% (68.81%): H:4.75% (5 05%): N:1.95% (1.91%).

EXAMPLE 11

Preparation of Bis(triphenylphosphoranylidene) Ammonium Trifluoromethane Sulfonate by Exchange Method A solution containing BTPPN-Cl, about 1.0 mmole, and lithium trifluoromethane sulfonate, about 3.0 mmoles, in about 3.0 grams methanol is added dropwise to about 100 ml stirred water.

A precipitate is formed which is collected by filtration and dried under vacuum for a yield of about 93 percent of a white powder.

Elemental analysis of the product gives actual (calculated) results of C:70.09% (66.76%); H:4.58% (4.39%): N:2.22% (2.05%).

The products of Examples 1–11 are evaluated for catalytic activity by Differential Scanning Calorimetry (DSC) with a DuPont 1090 Thermal Analyzer scanning at a rate of about 10° C./minute with an initiator/catalyst level of about 0.00157 mmoles/gram and a sample size of about 10 to 30 milligrams. A sample of the catalyst/initiator whose activity is to be characterized is dissolved in an appropriate solvent, preferably methylene chloride or methanol, in an amount to give a solution with a catalyst/initiator concentration of about 0.157 mmole/g. A stock evaluation solution is prepared by mixing epoxy resin DER-332 (diglycidyl ether of bisphenol A), about 57.5 g, bisphenol A polycarbonate resin, about 42.5 g, and methylene chloride, about 400 g. To a 10.0 g aliquot of the stock evaluation solution is added about 200 mg of catalyst/initiator solution, which results in a catalyst/initiator concentration of about 0.0157 mmole/g based on solids content. A glass slide is cleaned with methylene chloride and dried. A few milliliters of the catalyzed test solution is placed on a slide and the solvent allowed to evaporate. Residual solvent is removed from the resultant film by heating at about 50° C. for 30 minutes. The sample is scraped off the slide and a 10–30 mg portion placed in an aluminum DSC pan and sealed. An example of a DSC curve is illustrated by FIG. 1 for bis(triphenylphosphoranylidene) ammonium methane sulfonate. Temperature is shown on the x-axis and heat flow is shown on the y-axis. A peak indicates that an exothermic transition, in this case a chemical reaction, is taking place beginning at the temperature where the heat flow deviates from the baseline. The area under the peak is related to the total heat evolved and thus the heat of reaction and effectiveness of the catalyst. A secant line is drawn to the initial portion of the exothermic peak and extended to where it intersects the interpolated baseline. This defines the "secant onset temperature," which is the most reproducible comparative temperature reflecting where the reaction is just perceptibly beginning. This value reflects the upper processing temperature to ensure minimal reaction during blending and processing. For further details of the DSC test method, see DuPont 1090 *Thermal Analyzer Operator's Manual*, DuPont, Analytical Instruments Division, Concord Plaza-McKean Building, Wilmington, Del., 19898, May 1982, the relevant portions incorporated herein by reference for all legal purposes served thereby. Results are reported in Table I.

TABLE I
BIS(TRIPHENYLPHOSPHORANYLIDENE) AMMONIUM INITIATORS/CATALYSTS

| | | Exotherm | | |
|---|---|---|---|---|
| Example | Anion | Secant on-set (°C.) | Peak (°C.) | ΔHo (joules/gram) |
| 1 | hexafluorophosphate $PF_6$ | 193 | 236 | 253 |
| 2 | dihydrogen phosphate $H_2PO_4$ | 150 | 172 | 263 |
| 3 | hydrogen sulfate $HSO_4$ | 133 | 167 | 304 |
| 4 | trifluoroacetate $CF_3SO_3$ | 156 | 168 | 304 |
| 6 | p-toluensulfimidate $(CH_3C_6H_4SO_2)_2N$ | 143 | 166 | 274 |
| 7 | methane sulfonate $CH_3SO_3$ | 150 | 180 | 271 |
| 8 | p-toluene sulfonate | 166 | 195 | 261 |
| 9 | benzene sulfonate $C_6H_5SO_3$ | 163 | 199 | 272 |
| 10 | Cholrobenzene sulfonate $C_6H_4ClSO_3$ | 174 | 217 | 252 |
| 11 | trifluoromethane sulfonate $CF_3SO_3$ | 203 | 249 | 218 |

EXAMPLE 12

Initiator/Catalyst Use in Oxirane/Carbonate Reactions

A solution is prepared by dissolving bisphenol A polycarbonate, about 4.25 g (3.94 mmole/g carbonate linkages, 16.745 mmoles carbonate linkages) and about 5.75 g epoxy resin DER-332 (diglycidyl ether of bisphenol A, DGEBA) (5.75 mmole/g epoxy groups, 33.0625 mmoles epoxy groups, 1:1 stoichiometry based on two epoxide groups reacting with each carbonate linkage) in about 40.0 g methylene chloride. A second solution is prepared by dissolving bis (triphenylphosphoranylidene) ammonium benzenesulfonate, PNP-BS, about 0.0307 g, in about 0.25 g methylene chloride. To a 10.0 g aliquot of the first solution is added about 200 mg of the second solution, which gives a PNP-BS initiator concentration of about 0.0157 mmole/g on a solids basis. This combined epoxy resin/polycarbonate/initiator solution is cast onto a glass plate and the solvent allowed to evaporate over a period of 60 minutes. The resultant film is heated at about 50° C. for about 30 minutes to remove solvent, then cured at about 180° C. for about 2 hours followed by about 200° C. for about 4 hours. The cured film coating is clear, hard, and insoluble in methylene chloride.

EXAMPLE 13

Initiator/Catalyst Use in Oxirane/Ester Reactions

A solution is prepared by dissolving an aromatic copolyestercarbonate (prepared from bisphenol A, phosgene, and tere- and iso-phthaloyl chlorides such that the mole ratio of ester to carbonate linkages is 3/1 and the ratio of terephthaloyl to isophthaloyl residues is 4/1) which has an epoxy reactive equivalent weight of 81.13 based on one epoxy group reacting with each ester linkage and two epoxy groups reacting with each carbonate linkage, about 4.92 g, and about 5.08 g epoxy resin Tactix 742 (polyglycidyl ether of a tris (hydroxyphenyl)methane-based polyphenolic novolac resin), having an epoxide equivalent weight (EEW) of 160 (6.25 mmole/g epoxy groups, 1:1 stoichiometry based on two epoxide groups reacting with each carbonate linkage and one with each ester) in about 40.0 g methylene chloride. A second solution is prepared by dissolving bis(triphenylphosphoranylidene) ammonium benzenesulfonate, PNP-BS, about 0.0307 g, in about 0.25 g methylene chloride. To a 10.0 g aliquot of the first solution is added about 200 mg of the second solution, which gives a PNP-BS initiator concentration of about 0.0157 mmole/g on a solids basis. This combined epoxy resin/polyestercarbonate/initiator solution is cast onto a glass plate and the solvent allowed to evaporate over a period of 60 minutes. The resultant film is heated at about 50° C. for about 30 minutes to remove solvent, then cured at about 180° C. for about 2 hours followed by about 200° C. for about 4 hours. The cured film coating is clear, hard, and insoluble in methylene chloride.

What is claimed is:

1. A novel bis(phosphoranylidene) ammonium salt which exhibits activity as a catalyst/initiator, consisting essentially of a compound of the formula

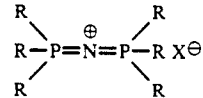

wherein

R is independently in each occurrence a $C_{1-20}$ monovalent hydrocarbon radical; and X is an anion selected from the group consisting of: $R^1SO_3^\ominus$, and $(R^3SO_2)_2N^\ominus$.

wherein $R^1$ is a $C_{1-12}$ monovalent hydrocarbon radical or $C_{1-12}$ monovalent halohydrocarbon radical, and $R^3$ is a $C_{1-12}$ monovalent hydrocarbon radical.

2. The bis(phosphoranylidene) ammonium salt of claim 1 wherein $R^1$ is a monovalent radical of a $C_{1-12}$ alkyl, $C_{1-12}$ haloalkyl, $C_{3-12}$ cycloalkyl, $C_{3-12}$ halocycloalkyl, $C_{6-12}$ alkylaryl, $C_{6-12}$ haloalkylaryl, $C_{6-12}$ aryl, or $C_{6-12}$ haloaryl, and $R^3$ is a monovalent radical of a $C_{1-12}$ alkyl, $C_{3-12}$ cycloalkyl, $C_{6-12}$ alkylaryl, or $C_{6-12}$ aryl.

3. The bis(phosphoranylidene) ammonium salt of claim 2 wherein $R^1$ is a monovalent radical of a $C_{1-6}$ alkyl, $C_{1-6}$ haloalkyl, $C_{6-12}$ alkylaryl, $C_{6-12}$ haloalkylaryl, phenyl, or halophenyl, and $R^3$ is a monovalent radical of a $C_{1-6}$ alkyl, $C_{6-12}$ alkylaryl, or phenyl.

4. The bis(phosphoranylidene) ammonium salt of claim 3 wherein $R^1$ is a monovalent radical of $C_{1-6}$ chloroalkyl, $C_{6-12}$ chloroalylaryl, or chlorophenyl.

5. The bis(phosphoranylidene) ammonium salt of claim 3 wherein

R is independently in each occurrence a monovalent radical of a $C_{1-12}$ alkyl, $C_{3-12}$ cycloalkyl, $C_{6-20}$ alkylaryl, or $C_{6-12}$ aryl.

6. The bis(phosphoranylidene) ammonium salt of claim 5 wherein

R is independently in each occurrence a monovalent radical of a $C_{1-6}$ alkyl, $C_{6-12}$ alkylaryl, or phenyl.

7. The bis(phosphoranylidene) ammonium salt of claim 6 wherein

R is independently in each occurrence a $C_{1-4}$ alkyl, $C_{6-8}$ alkylaryl, or phenyl radical.

8. The bis(phosphoranylidene) ammonium salt of claim 7 wherein

R is independently in each occurrence ethyl, butyl, or phenyl radical.

9. The bis(phosphoranylidene) ammonium salt of claim 8 wherein the onset of said activity begins at a temperature of above about 125° C.

10. The bis(phosphoranylidene) ammonium salt of claim 9 wherein said activity is substantially developed at a temperature below about 320° C.

* * * * *